United States Patent [19]

Truglio

[11] Patent Number: 4,709,705
[45] Date of Patent: Dec. 1, 1987

[54] LAVAGE DEVICE FOR OBTAINING A FLUID SPECIMEN FROM A BODY CAVITY FOR DISEASE DIAGNOSIS

[75] Inventor: Diana Truglio, Sayville, N.Y.

[73] Assignee: Medtech Diagnostics Inc., New York, N.Y.

[21] Appl. No.: 8,956

[22] Filed: Jan. 30, 1987

Related U.S. Application Data

[63] Continuation-in-part of Ser. No. 768,052, Aug. 22, 1985, abandoned.

[51] Int. Cl.⁴ ............................................. A61B 10/00
[52] U.S. Cl. .................................... 128/750; 604/37; 604/38; 604/45
[58] Field of Search ............................... 128/749–750; 604/36–42, 43, 45

[56] References Cited

U.S. PATENT DOCUMENTS

| 195,868 | 10/1877 | Woodward | 604/37 |
|---|---|---|---|
| 693,358 | 2/1902 | Westlake | 604/39 |
| 743,662 | 11/1903 | Ruckstuhl | 604/39 X |
| 1,526,313 | 2/1925 | Blakeslee | 604/39 X |
| 1,591,410 | 7/1926 | Spang | 604/40 |
| 2,147,652 | 10/1931 | Kennison | 604/39 X |
| 2,204,654 | 6/1940 | Booty | 604/37 |
| 2,576,766 | 11/1951 | Sokolik | 604/37 |
| 3,626,928 | 12/1971 | Barringer et al. | 128/750 |
| 3,785,366 | 1/1974 | Davis . | |
| 3,892,226 | 7/1975 | Rosen | 128/750 |
| 4,221,225 | 9/1980 | Sloan | 128/750 |
| 4,230,111 | 10/1980 | Piazza et al. | 604/55 |
| 4,294,251 | 10/1981 | Greenwald | 604/39 X |
| 4,490,138 | 12/1984 | Lipsky et al. | 604/40 |

Primary Examiner—William E. Kamm
Assistant Examiner—Angela D. Sykes
Attorney, Agent, or Firm—Spencer & Frank

[57] ABSTRACT

A lavage for obtaining a fluid specimen from a body cavity, has an elongated, flexible, narrow first tube insertable into a body cavity. A compressible bellows contains a saline solution communicating with the tube for ejecting the solution into the body cavity. A second tube surrounds the first tube and is insertable therewith into the body cavity to receive the solution expelled from the body. A third tube, attached to the first tube, communicates with the second tube to pass the expelled solution thereto. A removable cap on the third tube carries the second tube and serves as a stop member to limit insertion of the first and second tubes into the body cavity.

15 Claims, 12 Drawing Figures

LAVAGE DEVICE FOR OBTAINING A FLUID SPECIMEN FROM A BODY CAVITY FOR DISEASE DIAGNOSIS

BACKGROUND OF THE INVENTION

The present invention is a continuation-in-part application of Application Ser. No. 768,052 by the same inventor entitled "Lavage for Obtaining a Fluid Specimen from a Body Cavity for Disease Diagnosis", filed in the U.S. on Aug. 22nd, 1985, now abandoed.

FIELD OF THE INVENTION

This invention relates to a device for collecting fluid specimens from a body cavity, particularly a human body cavity, for laboratory examination. More particularly, this invention concerns a lavage device which facilitates recovering a fluid sample or a lavage medium after it has irrigated a vaginal area.

This device is useful for the simple collection of samples by a patient or a health practitioner for subsequent laboratory testing for diseases such as cervical cancer.

BACKGROUND OF THE INVENTION

A need has long existed for a device which can be used by an unskilled person, preferably by a patient herself, for obtaining a sample of cells from the vaginal area, to be examined in a clinical laboratory for the presence of abnormalities.

Devices known and used for this purpose, such as that which is described in U.S. Pat. No. 3,785,366 for example, require handling by a trained nurse or technician, are complex, and expensive.

SUMMARY OF THE INVENTION

The present invention enables the procurement of cell samples from body cavities, particularly vaginal samples, by an untrained person, even by a patient.

The present invention provides a sampling device containing a lavage medium, particularly a saline solution, which can be ejected intravaginally to wash the vaginal cavity therewith, and in the process of so doing mix the lavage medium with cells present therein.

Once inserted in the vaginal cavity, the lavage medium is expelled by natural action of the body into a container structure forming part of the sampling device which is removed from the inserted end of the device charged with expelling the lavage medium therefrom.

This structure can further be used as a shipping container for transporting the fluid liquid specimen to a clinical laboratory for examination and diagnosis.

More specifically, the sampling device of the invention comprises a first member comprising an elongated first tube having opposing first and second ends, said first end being insertable into a body cavity and said first tube having at least one lateral opening close to said first end and capable of discharging a lavage medium radially therefrom, and means forming a variable volume chamber for containing the lavage medium to irrigate the inside of the body cavity, said chamber being attached in sealing relationship to said second end of said first tube and communicating with the interior of said first tube; and a second member comprising means forming a collection chamber having opposing first and second ends, said first end having vents and said second end being mounted at, and in sealing relationship onto and around, said first tube near said means forming a variable volume, and an elongated second tube having opposing first and second ends, said first end being open and said second tube being shorter than, concentric with, surrounding and radially spaced from said first tube, to define a passage therebetween for the lavage medium to reenter the device through said first end of said second tube when the lavage medium is expelled from the body cavity, said second tube being insertable into the body cavity, said first end of said second tube being positioned at a distance from said first end of said first tube, and said second end of said second tube being in flow communication with said first end of said means forming a collection chamber so as to transfer the lavage medium thereto.

These and other objects and many of the attendant advantages of this invention will be readily appreciated as the same becomes better understood by reference to the accompanying drawings.

BRIEF DESCRIPTION OF THE DRAWINGS

FIGS. 9 and 10 are side sectional views of a removable rounded tip and the end of the insertable tube of one of the embodiments of the invention. In FIG. 9, the tip is in an open position, wherein it can radially expell the lavage medium. In FIG. 10, the tip is in a closed position, wherein no medium can be expelled.

Other objects, advantages and features of the present invention will become apparent to those skilled in the art from the following discussion.

DESCRIPTION OF THE PREFERRED EMBODIMENTS

The sampling device has an elongated structure with an insertion tube at one end communicating with a chamber in the form of a bellows, a syringe or a squeezable compartment at the other end. The chamber contains washing solution, e.g., a saline solution.

An important advantage of the present invention is its simple structure, which renders it possible for a patient to use the device herself at home without requiring assistance by others.

A further advantage of the present invention is the low cost and light-weight all-plastic expendable structure of the device.

Still another advantage of the present invention is that the device provides simple and reliable means for obtaining an uncontaminated liquid specimen usable in laboratory tests.

Surrounding the insertion tube is a removable collection tube communicating with or attached to a collection chamber. The collection tube is removed from the device after a liquid specimen is internalized in the collection chamber and the device is removed from the body cavity.

The liquid specimen can then be poured into a prepared specimen tube which is then capped and shipped to a clinical laboratory for examination of the liquid specimen for disease diagnosis.

Alternatively, a cap may be applied to the collection chamber which may then serve as a shipping container.

Referring now to the drawings, wherein like reference characters designate like or corresponding parts throughout, FIGS. 1, 2, 3, 11 and 12 illustrate a lavage device generally designated by reference numeral 10.

The lavage device 10 comprises a narrow elongated, flexible plastic tube 12 having a rounded tip 14 at one end to facilitate the insertion of the tube into a body cavity. The top of the tube 12 has lateral hole(s) 16 for ejecting a liquid 18, e.g. saline, from the tube 12.

The lateral hole(s) 16 prevents the liquid 18 from being expelled axially from the tube. The tube 12 extends axially downward and is connected to a cylindrical neck 20 of an axially compressible plastic bellows 22 or a syringe-like chamber 69 provided with a piston 70.

A bellows chamber 21 of the bellows 22 or the syringe-like chamber 69 is filled at the factory, prior to shipment of the device, with a liquid 18, e.g., a normal saline solution which is about nine parts salt per thousand parts water.

The saline solution or liquid 18 is ejected from the bellows 22 or the syringe-like chamber 69 and out of the tube 12 when the bellows 22 or the piston 70 is compressed axially.

Surrounding the tube 12 is a cylindrical tube or chamber 24, which is axially parallel to the tube 12 and concentric with it. The tube 24 has a narrow bottom-closed end 23 secured to and encircling the tube 12. The tube 24 is open at an upper wide end 25.

In one embodiment of the invention, an external thread 26 (FIGS. 1, 2 and 6) at the upper end 25 of the tube 24 engages an internal thread 28 of a removable screw cap 30. The thread 28 of the cap 30 is loosely mated to the thread 26 of the tube 24 to vent the inside of the tube or chamber 24 when it is being filled as will hereinafter be more specifically described. The cap 30 is formed with an internal groove 32 which snugly receives the upper end 25 of the tube 24.

Figure 1:
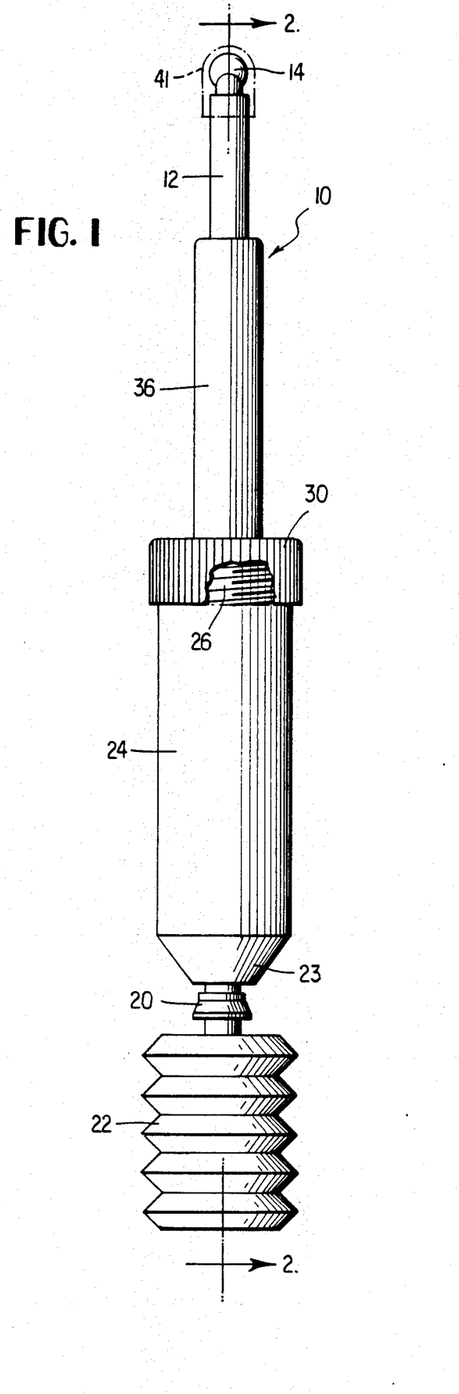
FIG. 1 is a side elevational view of a lavage device embodying the present invention.
Figure 2:
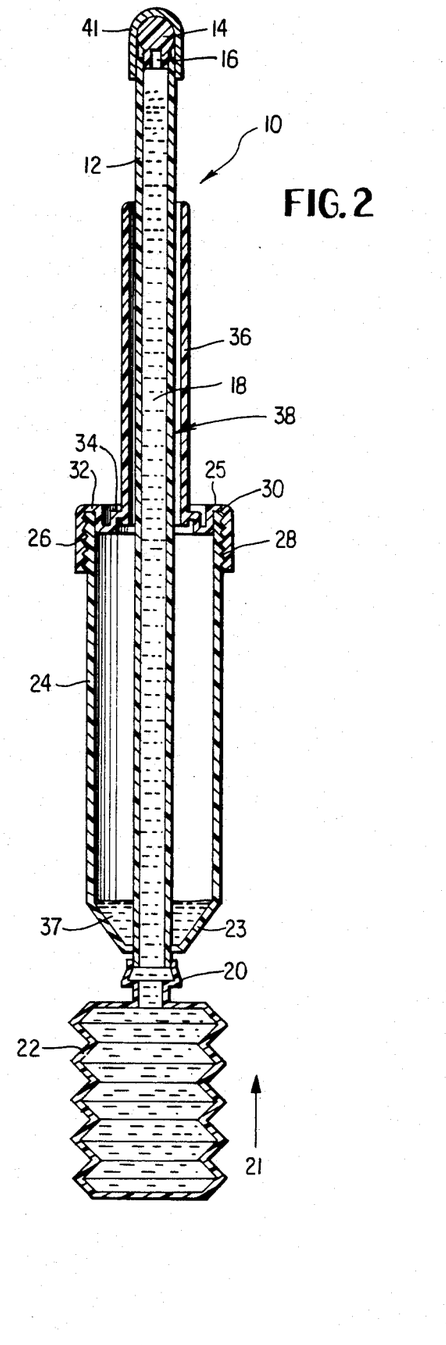
FIG. 2 is an axial sectional view taken along line 2—2 of FIG. 1.
Figure 6:
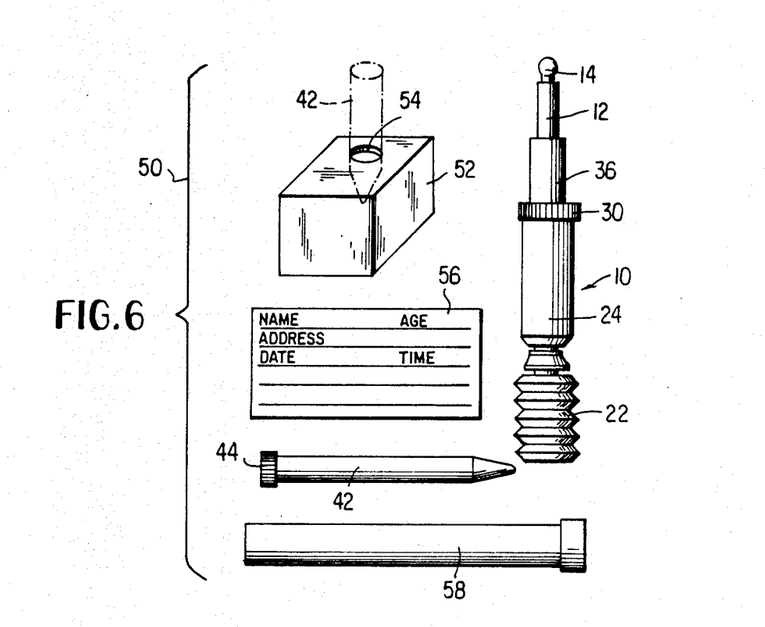
FIG. 6 is a view on a reduced scale of parts of a kit including the lavage device embodying the invention.

The cap 30 has a central hole 34 in which is fitted the bottom end of another cylindrical tube 36 open at its top and bottom ends and surrounding an upper portion of the tube 12 (FIGS. 1, 2 and 6).

The internal diameter of the tube 36 is larger than the external diameter of the tube 12 to define a passsage 38 through which an expelled liquid 18' from the body cavity can flow into the tube or chamber 24.

A certain distance must exist between the insertable end of the tube 12 containing the hole(s) 16 and the closest open end of the tube 36. This distance is designed so that when the liquid 18 is expelled from the device, it can become in contact with the tissues to be lavaged to gather samples of cells therefrom or of materials deposited on the surfaces thereof prior to being returned to the device through the opening 38 of the tube 36 for collection in the chamber 24. This is a critical feature which renders the device superior to any other device known prior to this invention.

Figure 3:
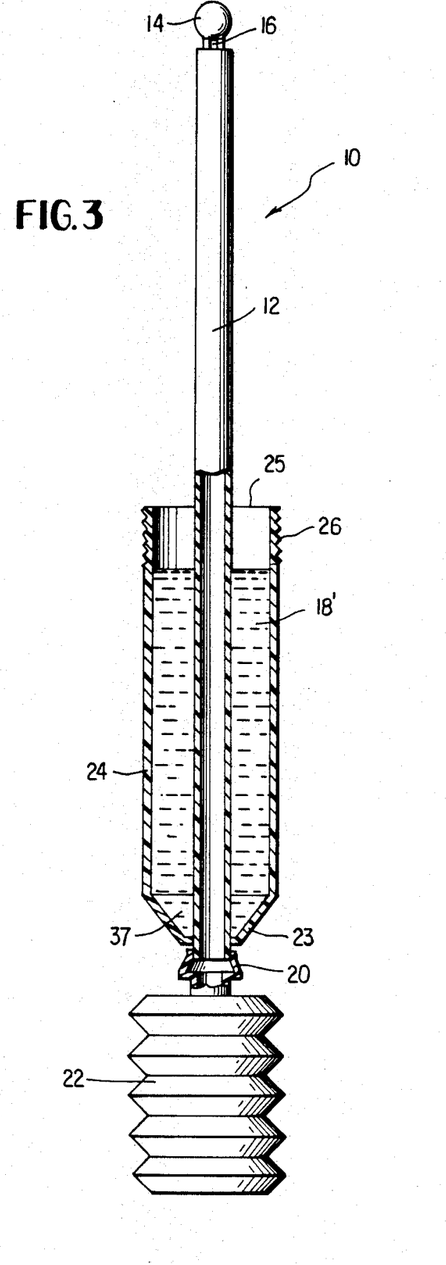
FIG. 3 is an axial sectional view similar to FIG. 2, with the collection tube and cap removed from the device which is filled with the expelled liquid.
Figure 11:
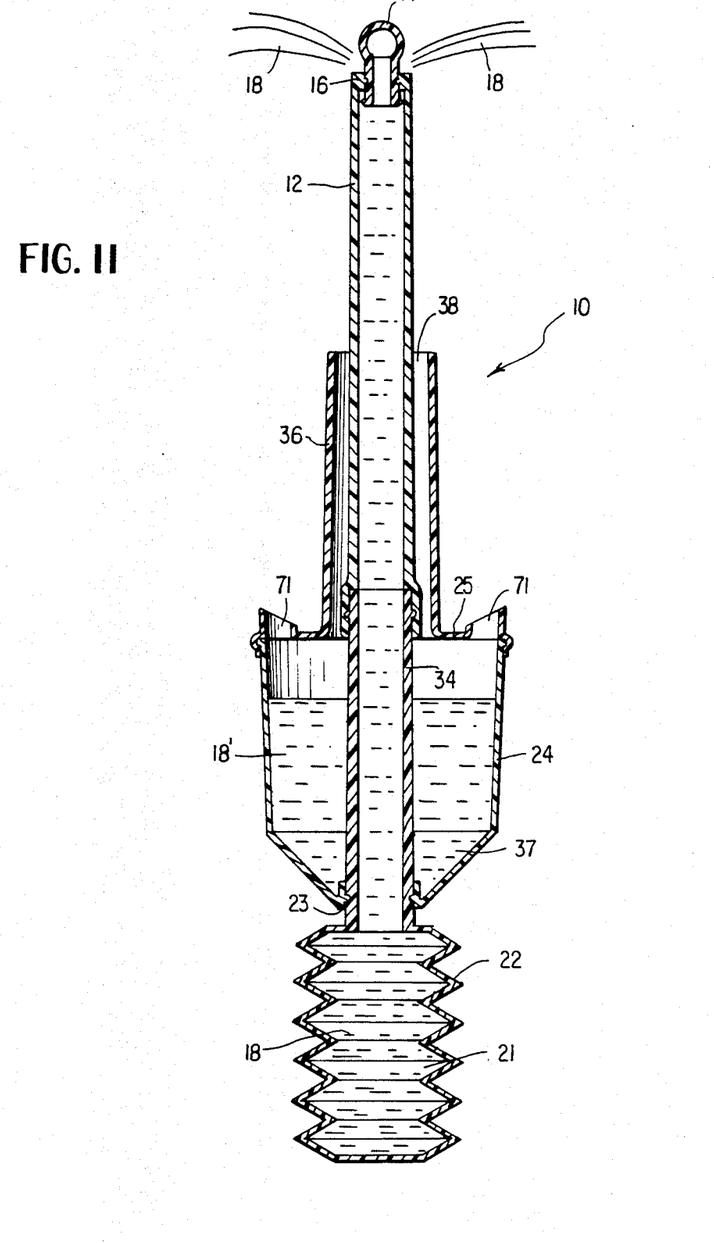
FIG. 11 is a side sectional view of another embodiment of the invention wherein the compressible chamber is in the form of a bellows.
Figure 12:
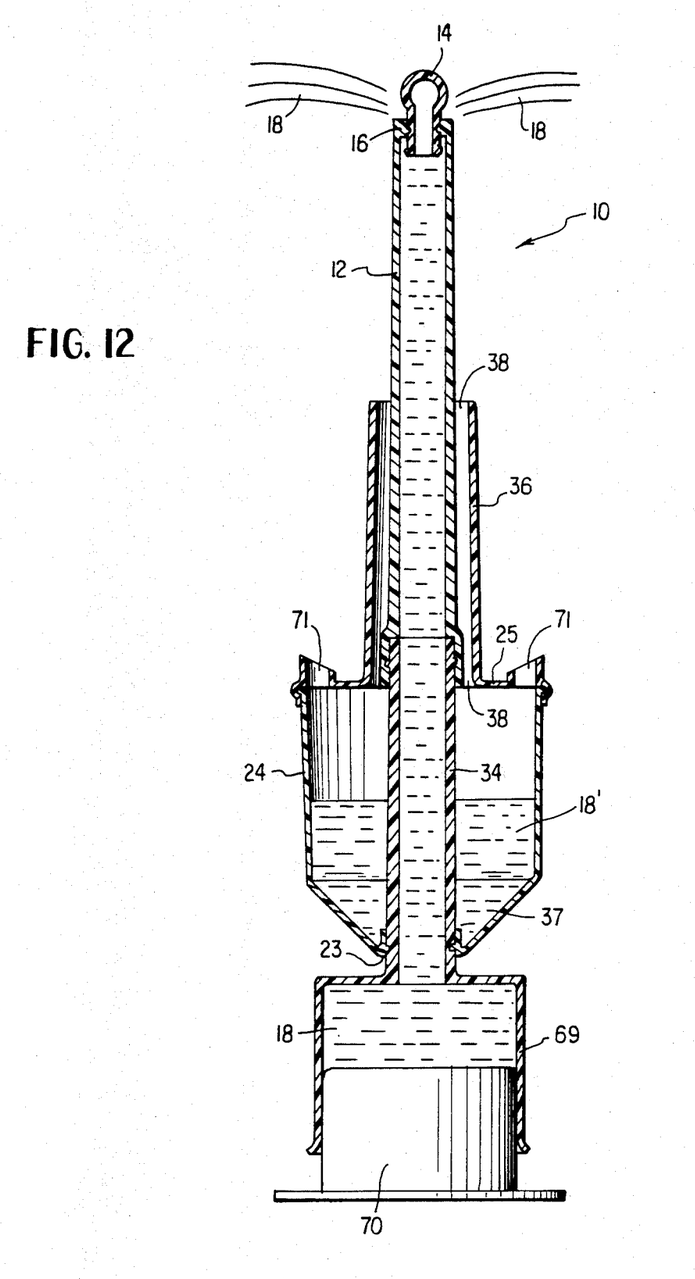
FIG. 12 is a side sectional view of another embodiment of the invention wherein the compressible chamber has a syringe-like structure.

If desired the tube 24 may contain a preservative such as a liquid 37 (FIG. 2) for the expelled liquid 18' shown in FIGS. 3, 11 and 12.

In another embodiment of the invention, the chamber 24 and the tube 36 are directly connected to each other as shown in FIGS. 11 and 12. The design of this embodiment of the device does away with the need for a screw cap used in an alternative embodiment described above.

The opening at the upper wide end 25 of the tube 24 takes the form of one or more vents 71 to permit the filling of the chamber 24 (FIGS. 11 and 12).

As indicated in FIGS. 11 and 12, the chamber 24 and the tube 36 are in flow communication therebetween. The internal diameter of the tube 36 is made to be larger than the external diameter of the tube 12, thereby defining the passage 38.

FIGS. 1, 2, 11 and 12 show the device 10 in condition for use. The user assumes a convenient, comfortable sitting or standing position. She then removes a tape 41 (FIG. 1) which seals and maintains the sterility of the tip 14 and the top of the tube 12, thus readying the device for use.

The tube 12 and the tube 36 are then gently inserted axially into the vagina of the patient until the knurled or fluted cap 30 or the upper end 25 of the tube 24 contacts the vagina.

The bellows 22 are then squeezed or the piston 70 is pressed axially upward to eject the liquid 18 through the tube 12 and into the vagina through the hole(s) 16 to provide a radial washing pattern.

The liquid 18 will thus wash or irrigate the interior of the vagina and will then naturally flow from the vagina into the tube 36 located at a distance away from the hole(s) 16 through the passage 38 and into the chamber 24.

As the expelled liquid 18' fills the chamber 24, air is vented to the atmosphere via the vents 71 (FIGS. 11 and 12) or the loose fit between the threads 28 of the cap 30 and the threads 26 (FIGS. 1 and 2) of the chamber 24.

Figure 4:
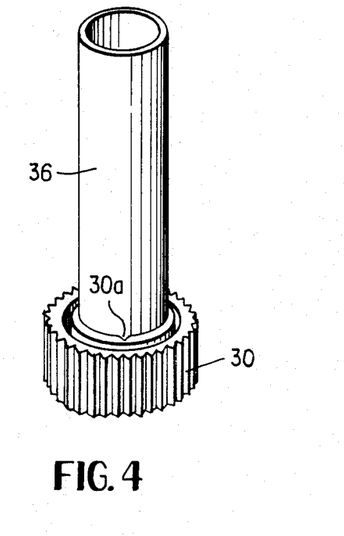
FIG. 4 is an oblique view of the collection tube.

If desired, the top of the cap 30 may have one or more orifices, such as 30a, illustrated in FIG. 4, to vent the chamber 24.

The expelled liquid 18' collects and fills the chamber 24 as shown in FIG. 3. The tube 36 serves as a collection tube and the tube 24 serves as a well or chamber for the liquid 18'. As indicated supra, a liquid preservative 37 can be provided in the tube 24.

The device 10 can then be removed from the vagina.

In one of the embodiments, the cap 30 is then unscrewed, and the tube 36 with the cap 30 is removed by lifting the tube 36 axially upward from the tube 12 in one of the embodiments. FIG. 4 shows the removed collection tube 36 with the attached cap 30.

FIG. 3 shows the device 10 after removal of the collection tube 36, with the expelled liquid 18' filling the tube or chamber 24.

Figure 5:
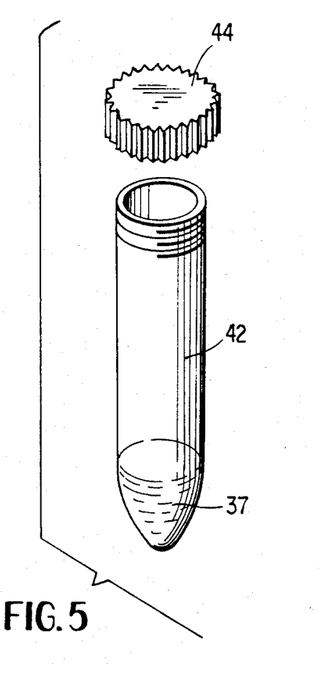
FIG. 5 is a reduced exploded oblique view of a specimen container and cap.

FIG. 5 shows a specimen tube 42 containing a liquid preservative 37 into which the liquid 18' can be poured from the chamber 24. The tube 42 may be sealed by a screw cap 44.

FIG. 6 shows parts of a specimen collection kit 50 which can be supplied to the user. In addition to the lavage device 10, the kit includes a box 52 having a hole 54 in the top, through which the specimen tube 42 may be inserted with the cap 44 removed and ready for receiving the expelled liquid 18' from the device 10.

The kit 50 further includes a card 56 onto which the user can write pertinent information concerning herself and the specimen.

A mailing tube 58 is provided for shipping the specimen tube and card to a clinical laboratory. The device is to be discarded after a single use.

Figure 9:
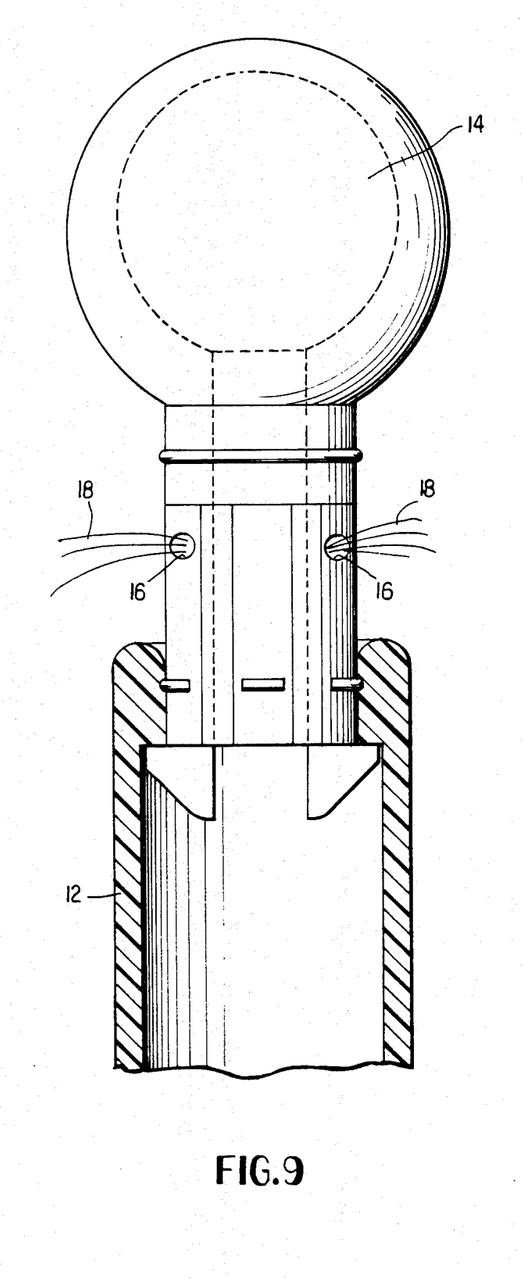
Figure 10:
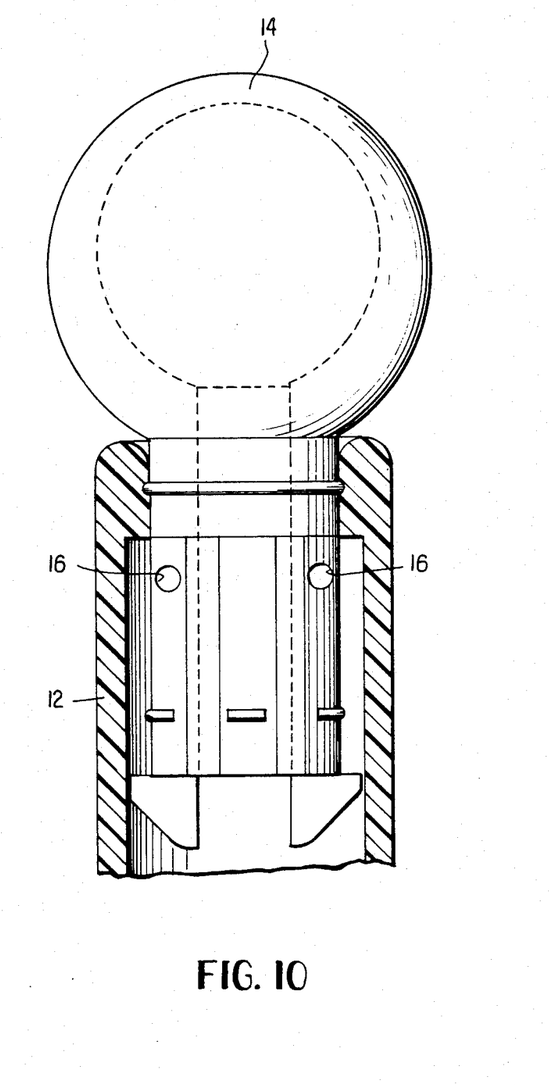

FIGS. 9, 10, 11 and 12 show a different embodiment of the invention having a tube 12 containing a separate rounded tip 14. This tip 14 can be inserted into the tube 12 in at least two positions which are shown in FIGS. 9 and 10.

In a first position, shown in FIG. 9, the rounded tip 14 is partially removed from the tube 12, thereby exposing the hole(s) 16 through which liquid can be expelled.

In a second position, shown in FIG. 10, the rounded tip 14 is fully inserted in the tube 12, thereby not permitting the free exposure of the hole(s) 16 and precluding the flow of fluid out of the device.

It may be desirable to avoid the transfer of the collected liquid 18' out of tube 24 to prevent spillage, contamination, and the like. For this purpose a special cap 60 shown in FIGS. 7 and 8 may be provided for the tube 24.

Figure 7:
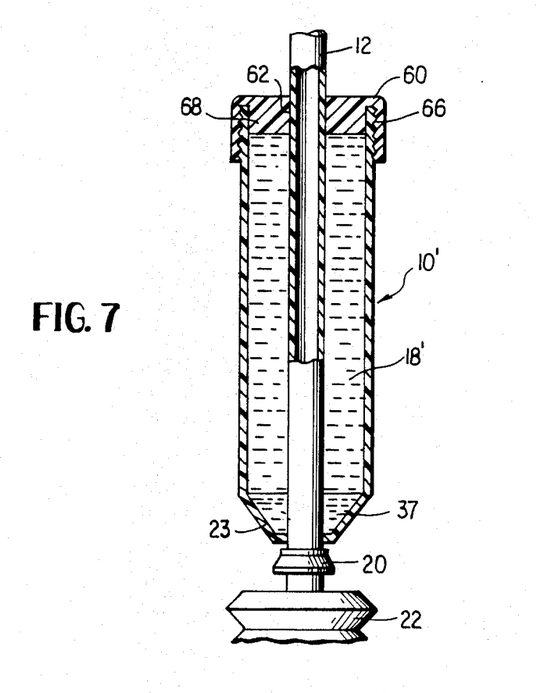
FIG. 7 is a fragmentary sectional view similar to a portion of FIG. 3, showing the lavage device filled with expelled liquid and capped for shipment.
Figure 8:
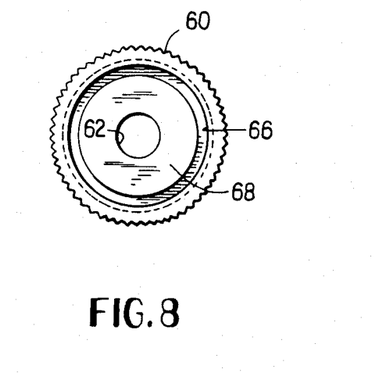
FIG. 8 is a top view of the lavage device of FIG. 7.

The cap 60 is made of resilient plastic or artificial rubber and has a central hole 62, whose rim frictionally grips and seals the tube 12 passing therethrough.

The cap 60 may have an internal threading 66 which securely grips and mates with the threaded top of the tube 24, or it may simply tightly fit around the tube 24 to prevent any leakage therefrom.

A central annular plug 68 at the underside of the cap 60 seals the top of the tube 24. The sealed device 10' as shown in FIG. 7 may now be inserted into a protective mailing tube and shipped to a clinical laboratory.

In this embodiment, the liquid preservative 37 must be present in the tube 24 to maintain the integrity of the specimen.

The present invention as described above, makes it possible to recover an irrigating solution such as saline after it has washed a vaginal area. This expelled solution may then be examined microscopically and/or by other standard procedures available at qualified clinical laboratories.

The invention makes possible the detection of abnormal cells at an early stage of development since the specimen collection can be done by a patient in the privacy of the home.

The early detection of the presence of abnormal cells in the vaginal area can alert the user to obtain appropriate medical treatment before such condition becomes dangerous.

It should be understood that the foregoing description relates solely to a limited number of preferred embodiments of the invention which have been provided by way of example only, and that it is intended to cover all changes and modifications of the examples of the invention herein chosen for the purpose of the disclosure which do not constitute departures from the spirit and scope of the invention.

The present disclosure relates to the subject matter disclosed in U.S. Application Ser. No. 768,052 filed on Aug. 22nd, 1985, now abandoned, the entire specification of which is incorporated herein by reference.

What is claimed is:

1. A lavage device for obtaining a fluid specimen from a body cavity, said device comprising a first member comprising
an elongated first tube having opposing first and second ends, said first end being insertable into a body cavity and said first tube having at least one lateral opening close to said first end and capable of discharging a lavage medium radially therefrom; and
means forming a variable volume chamber for containing the lavage medium to irrigate the inside of the body cavity, said chamber being attached in sealing relationship to said second end of said first tube and communicating with the interior of said first tube; and a second member comprising
means forming a collection chamber having opposing first and second ends, said first end having vents and said second end being mounted at, and in sealing relationship onto and around, said first tube near said means forming a variable volume; and
an elongated second tube having opposing first and second ends, said first end being open and said second tube being shorter than, concentric with, surrounding and radially spaced from said first tube, to define a passage therebetween for the lavage medium to reenter the device through said first end of said second tube when the lavage medium is expelled from the body cavity, said second tube being insertable into the body cavity, said first end of said second tube being positioned at a distance from said first end of said first tube, and said second end of said second tube being in flow communication with said first end of said means forming a collection chamber so as to transfer the lavage medium thereto.

2. The device of claim 1, wherein
said first tube has a rounded tip positioned at said first end of said first tube to facilitate the insertion of said device into the body cavity; and the lateral opening of said first tube is positioned near said tip.

3. The device of claim 2, wherein
said first end of said first tube is open;
said rounded tip contains said lateral opening and is removably insertable into said first end of said first tube and in sealing relationship thereto; and
said rounded tip is insertable into said first tube in a position selected from a first position in which said lateral opening is sealed for collecting a fluid sample without expelling any lavage medium, and a second position in which said lateral opening is exposed for radially expelling the lavage medium.

4. The device of claim 1, wherein
said means forming a variable volume chamber has the form of a bellows which is axially compressible to expel the lavage medium therefrom.

5. The device of claim 1, wherein
said means forming a variable volume chamber is provided with a piston for axially expelling the lavage medium therefrom.

6. The device of claim 1, wherein
said first tube is provided with a plurality of lateral openings arranged annularly.

7. The device of claim 1, further comprising
a first cap removably mounted on said first end of said means forming a collection chamber for closing said collection chamber, and wherein said second end of said second tube is secured to said first cap and removable therewith from said means forming a collection chamber.

8. The device of claim 7, wherein
said first cap extends radially beyond said means forming a collection chamber to axially limit the insertion of said device into the body cavity to the length of said first and second tubes and to prevent leakage from the body cavity during aspiration of the lavage medium into said second tube.

9. The device of claim 7, wherein
said first cap is further provided with an aperture through which said first tube extends.

10. The device of claim 7, further comprising
a second cap detachably mounted on said means forming a collection chamber for closing said collection chamber after collecting a fluid sample and removing said second tube and said first cap, said second cap being further provided with an aperture through which said first tube extends in sealing relationship thereat; and a plug detachably mountable between said means forming a collection chamber and said second cap and in sealing relationship thereto when said means forming a collection chamber is closed.

11. The device of claim 1, wherein
said first cap has vents which are in flow communication with said vents of said means forming a variable volume chamber.

12. The device of claim 1, wherein
said first and second tubes and said means forming a collection chamber are cylindrical.

13. The device of claim 1, wherein
said second end of said means forming a variable volume chamber is detachably mounted on said first tube.

14. The device of claim 1, wherein
said collection chamber further contains a preserving medium.

15. The device of claim 1, wherein
said variable volume chamber further contains a saline solution.

* * * * *